United States Patent [19]

Caufield

[11] Patent Number: 5,378,696
[45] Date of Patent: * Jan. 3, 1995

[54] RAPAMYCIN ESTERS

[75] Inventor: Craig E. Caufield, Plainsboro, N.J.

[73] Assignee: American Home Products Corporation, Madison, N.J.

[*] Notice: The portion of the term of this patent subsequent to Jun. 22, 2010 has been disclaimed.

[21] Appl. No.: 73,857

[22] Filed: Jun. 8, 1993

Related U.S. Application Data

[63] Continuation-in-part of Ser. No. 44,341, Apr. 7, 1993, which is a continuation of Ser. No. 777,983, Oct. 19, 1991, Pat. No. 5,221,670, which is a continuation-in-part of Ser. No. 584,833, Sep. 19, 1990, abandoned.

[51] Int. Cl.$^6$ .................. C07D 457/06; A61K 31/33
[52] U.S. Cl. ........................................ 514/183; 540/455
[58] Field of Search ........................... 540/455; 514/183

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,401,653 | 8/1983 | Eng | 424/122 |
| 4,650,803 | 3/1987 | Stella et al. | 514/291 |
| 4,885,171 | 12/1989 | Surendra et al. | 424/122 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield et al. | 514/291 |
| 5,118,677 | 6/1992 | Caufield | 514/183 |
| 5,118,678 | 6/1992 | Kao et al. | 514/183 |
| 5,120,842 | 6/1992 | Failli et al. | 514/321 |
| 5,130,307 | 7/1992 | Failli et al. | 514/321 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/542 |
| 5,221,670 | 6/1993 | Caufield | 514/183 |
| 5,233,036 | 8/1993 | Hughes | 540/455 |

FOREIGN PATENT DOCUMENTS

507555A1  3/1992  European Pat. Off. .
05031  11/1985  WIPO .

OTHER PUBLICATIONS

Huffer et al. "Introduction to Human Immunology" Jones & Bartlett Publish. p. 161, 1986.
Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, J. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L. Fifth Int. Conf. Inflamm. Res. Assoc. 121 (Abstract) (1990).
Gregory C. et al., J. Heart Lung Transplant 11 (pt 2): 197 (1992).
Stepkowski, S. M., Transplantation Proceedings 23(1): 507–508 (1991).

Primary Examiner—Celia Chang
Attorney, Agent, or Firm—Arnold S. Milowsky

[57]  ABSTRACT

A compound of the structure (List continued on next page.)

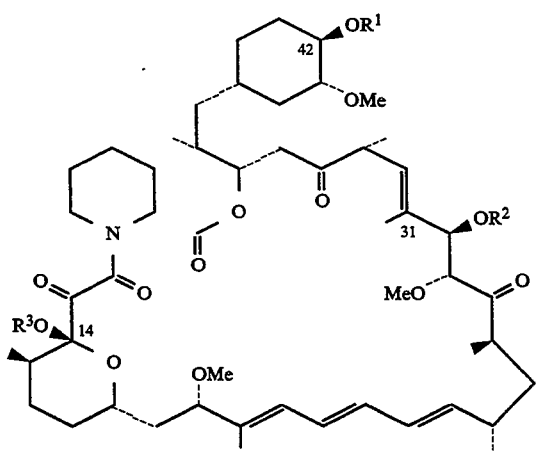

wherein
R¹, R², and R³ are each, independently, hydrogen or

with the proviso that R¹, R², and R³ are not all hydrogen;
R⁴ is —$(CH_2)_m X(CH_2)_n CO_2 R^5$ or

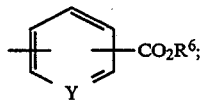

R⁵ and R⁶ are each, independently, hydrogen, alkyl, alkenyl, alkynyl, $(CH_2)_p NR^9 R^{10}$, mono-, di-, or tri-hydroxyalkyl, aralkyl, or aryl;

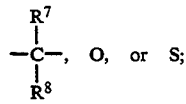

R⁷, R⁸, R⁹, and R¹⁰ are each, independently, hydrogen or alkyl;
Y is CH or N:
m is 0–4; n is 0–4; p is 0–4;
with the proviso that m and n are not both 0 when X is O or S;

or a pharmaceutically acceptable salt thereof, which is by virtue of its immunosuppressive activity is useful in treating transplantation rejection, host vs. graft disease, autoimmune diseases, and diseases of inflammation, by virtue of its antitumor activity useful in treating tumors, and by virtue of its antifungal activity is useful in treating fungal infections.

6 Claims, No Drawings

RAPAMYCIN ESTERS

CROSS REFERENCE TO RELATED APPLICATION

This application is a continuation in part of Ser. No. 08/044,341, filed Apr. 7, 1993, which is a continuation of Serial No. 07/777,983, filed Oct. 19, 1991, now U.S. Pat. No. 5,221,670, which is a continuation in part of Ser. No. 584,833, filed Sep. 19, 1990, abandoned.

BACKGROUND OF THE INVENTION

This invention relates to esters of rapamycin and a method for using them to induce immunosuppression, and in the treatment of transplantation rejection, host vs. graft disease, autoimmune diseases, diseases of inflammation, tumors, hyperproliferative vascular disorders, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3,929,992; and U.S. Pat. No. 3,993,749].

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], and ocular inflammation [European Patent Application 532,862 A 1].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, antitumor, antiproliferative, and antifungal agents having the structure

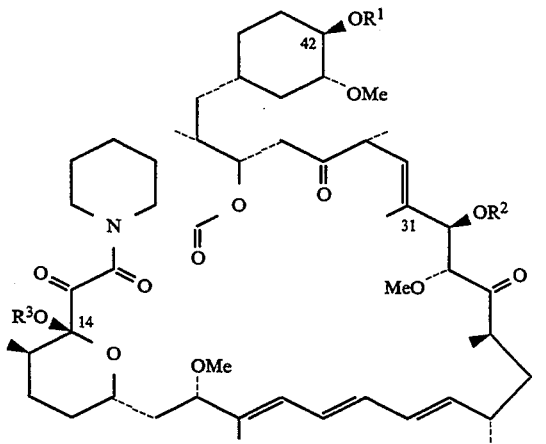

wherein
$R^1$, $R^2$, and $R^3$ are each, independently, hydrogen or

with the proviso that $R^1$, $R^2$, and $R^3$ are not all hydrogen;

$R^4$ is $—(CH_2)_mX(CH_2)_nCO_2R^5$ or

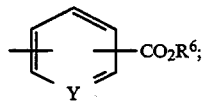

$R^5$ and $R^6$ are each, independently, hydrogen, alkyl of 1-6 carbon atoms, alkenyl of 2-7 carbon atoms, alkynyl of 2-7 carbon atoms, $(CH_2)_pNR^9R^{10}$, mono-, di-, or tri-hydroxyalkyl of 1-8 carbon atoms, alkyl of 7-10 carbon atoms, or aryl, which is optionally mono-, di-, or tri- substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, and alkylthio of 1-6 carbon atoms, and

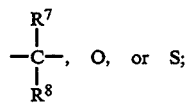

$R^7$, $R^8$, $R^9$, and $R$ are each, independently, hydrogen or alkyl of 1-carbon atoms;
Y is CH or N;
m is 0–4;
n is 0–4;
p is 1–4;
with the proviso that m and n are not both 0 when X is O or S;
or a pharmaceutically acceptable salt thereof.

Of the compounds, preferred members are those in which $R^4$ is —$(CH_2)X(CH_2)_nCO_2R^5$; and those in which $R^4$ is —$(CH_2)_mX(CH_2)_nCO_2R$ and $R^5$ is alkenyl of 2–7 carbon atoms.

Aryl is defined as an organic radical derived from an aromatic hydrocarbon by the removal of one atom; e.g., phenyl from benzene. Aralkyl is defined as an arylated alkyl radical; a radical in which an alkyl H atom is substituted by an aryl group. When the terms aryl or arylalkyl are used, it is preferred that the aryl moiety is a phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benz[b]thiophenolyl, benzimidazolyl, benzthiazolyl, benzodioxolyl, piperidinyl, morpholinyl, piperazinyl, tetrahydrofuranyl, or pyrrolidinyl group. The aryl moiety may be optionally mono-, di-, or tri-substituted with a group selected from alkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, and the like.

The pharmaceutically acceptable salts may be formed from inorganic cations such as sodium, potassium, and the like; mono-, di-, and trialkyl amines of 1–6 carbon atoms, per alkyl group and mono-, di-, and trihydroxyalkyl amines of 1–6 carbon atoms per alkyl group. Preferred salts are formed from sodium cations and tris(hydroxymethyl)methylamine.

The compounds of this invention can be prepared by acylating rapamycin with an acylating agent having the general structure

where X is OH, in the presence of a coupling reagent, such as dicyclohexylcarbodiimide. The compounds of this invention also can be prepared using an anhydride of the above described carboxylic acid as the acylating species. Alternatively, the acylating species can be an acid halide, where X can be Cl, Br, or I. The acylating groups used to prepare the compounds of this invention are commercially available or can be prepared by methods that are disclosed in the literature.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. inhibition of lymphoproliferation is assessed in percent change in counts per minute from non-drug treated controls. The results are expressed by the following ratio:

$$\frac{{}^3\text{H-control thymus cells} - {}^3\text{H-rapamycin-treated thymus cells}}{{}^3\text{H-control thymus cells} - {}^3\text{H-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Compounds evaluated in the PLN test procedure were administered orally, unless otherwise indicated, as being administered intraperitoneally. Carboxymethyl cellulose was used as the vehicle for administration, unless otherwise indicated. Results are expressed by the following ratio, unless otherwise indicated:

$$\frac{{}^3\text{H-PLN cells control C3H mouse} - {}^3\text{H-PLN cells rapamycin-treated C3H mouse}}{{}^3\text{H-PLN cells control C3H mouse} - {}^3\text{H-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these three standard test procedures.

TABLE 1

| Compound | LAF* (ratio) | PLN* (ratio) | Skin Graft (days + SD) |
|---|---|---|---|
| Example 1 | 0.37 | ++ | 8.2 ± 1.2 |
| Example 2 | 0.9 | 0.69** | 10.7 ± 1.2 |
| Example 3 | 3.27 | 1.04** 0.20 | 12.7 ± 0.9 |

TABLE 1-continued

| Compound | LAF* (ratio) | PLN* (ratio) | Skin Graft (days + SD) |
|---|---|---|---|
|  |  | 2.08 |  |
| Example 4 | 0.56 | 1.68 | 10.2 ± 1.7 |
|  |  | 0.42 |  |
| Example 5 | 0.02 | 1.11 | 8.0 ± 1.7 |
| Example 6 | 0.01 | 0.48 | 8.0 ± 0.9 |
| Example 7 | 0.97 | 0.70** | 12.0 ± 1.0 |
| Example 8 | 0.22 | −1.93 | 9.3 ± 1.6 |
|  |  | 0.37**,+ |  |
| Example 9 | 0.22 | 0.41 | 10.2 ± 1.2 |
| Example 10 | 0.18 | 0.39 | 10.8 ± 0.8 |
| Example 11 | 0.00 | 0.09 | 7.8 ± 1.7 |
| Example 12 | 97%+++ | 1.04 | 10.8 ± 0.4 |
| Example 13 | 2.11 | 1.02 | 10.6 ± 0.9 |
|  |  | 0.40 |  |
| Example 14 | 3.42 |  | 11.0 ± 0.0 |
| Example 15 | 0.40 |  | 9.8 ± 0.8 |
| Rapamycin | 1.0 | 1.0 | 12.0 ± 1.7 |

*Calculation of ratios was described supra.
**Administered using cremophore/ethanol as the vehicle.
+Administered intraperitoneally.
++Not evaluated.
+++Result expressed as percent inhibition at 100 nM.

The results of these standard pharmacological test procedures demonstrate immunosuppressive activity both in vitro and in vivo for the compounds of this invention. Positive ratios in the LAF and PLN test procedures indicate suppression of T cell proliferation. As a transplanted pinch skin grafts are typically rejected within 6–7 days without the use of an immunosuppressive agent, the increased survival time of the skin graft when treated with the compounds of this invention further demonstrates their utility as immunosuppressive agents. While it appears that the compound disclosed by Example 8 may cause T cell proliferation in the PLN test procedure because of the −1.93 ratio obtained, it is believed that this result is merely an anomaly in light of the other data obtained. Spurious results have been obtained in the PLN test procedure using compounds that have low bioavailability. Low bioavailability can be due to the compound itself, the dose used, the vehicle, the route of administration, or a combination of any of the above factors. When the negative ratio was obtained for the compound of Example 8, it was administered orally in carboxymethylcellulose. A negative ratio in the PLN test procedure was not observed for the compounds of Examples 9 and 10, which are pharmaceutical salts of the compound of Example 8. When the compound of Example 8 was administered i.p. in a mixture of cremophore and ethanol as the vehicle, a positive ratio was obtained indicating the compound had immunosuppressive activity. The positive ratio obtained in the LAF test procedure coupled with the increased survival time observed in the skin graft test procedure confirm the immunosuppressive activity of the compound of Example 8. The negative ratio obtained when the compound of Example 8 was administered orally in carboxymethyl cellulose is therefore believed to be attributed to low bioavailability, and not a function of its immunosuppressive activity.

Antifungal activity of the compounds of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC (μg/ml) to inhibit growth. The results of this test procedure showed that the compounds of this invention have antifungal activity; however, it was surprising that the compounds of this invention were less active that the parent compound, rapamycin. The compounds of Examples 12 and 13 were not evaluated for antifungal activity, but because of the structural similarity to the ones that were evaluated, they too are considered to have antifungal activity.

TABLE 2*

| Compound | Strain of *Candida albicans* | | | | |
|---|---|---|---|---|---|
|  | ATCC 10231 | ATCC 38246 | ATCC 38247 | ATCC 38248 | 3669 |
| Example 1 | >0.4 | >0.4 | >0.4 | >0.4 | >0.4 |
| Example 2 | >0.4 | 0.4 | >0.4 | 0.4 | 0.4 |
| Example 3 | 0.2 | 0.1 | 0.4 | 0.1 | 0.1 |
| Example 4 | >0.4 | 0.2 | >0.4 | 0.2 | 0.4 |
| Example 5 | 0.4 | >0.4 | >0.4 | >0.4 | >0.4 |
| Example 6 | 0.4 | >0.4 | 0.4 | >0.4 | >0.4 |
| Example 7 | 0.1 | 0.4 | 0.1 | 0.1 | 0.2 |
| Example 8 | 0.4 | >0.4 | 0.4 | >0.4 | >0.4 |
| Example 9 | 0.2 | >0.4 | 0.2 | 0.4 | >0.4 |
| Example 10 | 0.1 | >0.4 | 0.2 | 0.4 | >0.4 |
| Example 11 | >0.4 | >0.4 | >0.4 | >0.4 | >0.4 |
| Rapamycin | 0.003 | 0.025 | 0.003 | 0.006 | 0.025 |

*expressed as MIC (μg/ml)

Based on the results of these standard pharmacological test procedures, the compounds are useful in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; diseases of inflammation such as psoriasis, dermatitis, eczema, seborrhea, inflammatory bowel disease, pulmonary inflammation, asthma, and eye uveitis; and fungal infections. As the compounds of this invention are structurally related to rapamycin, which has antitumor activity, they too are considered to be useful as antitumor agents.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The compounds of this invention may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, gildants, compression aids, binders or tablet-disintegrating agents; it can also be an encapsulating material. In powders, the carder is a finely divided solid which is in admixture with the finely divided active ingredient. In tablets, the active ingredient is mixed with a career having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid career can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carder for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 µg/kg-100 mg/kg, preferably between 0.001-25 mg/kg, and more preferably between 0.01-5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds this invention.

EXAMPLE 1

Rapamycin- 14,31,42-tris(monobenzylsuccinate)

To a solution of 5.0 g (5.47 mmol) of rapamycin, 3.41 g (16.41 mmol) of monobenzylsuccinate, and 3.15 g (16.41 mmol) of 1-(3-dimethylaminopropyl)-3-ethylcarbodiimide hydrochloride in 20 mL of dry dichloromethane was added 200 mg of 4-dimethylaminopyridine. The solution was stirred at room temperature for 3 days. The reaction mixture was poured into 2N HCl and extracted three times with ethyl acetate. The organic layers were combined, washed with brine, dried over anhydrous sodium sulfate, decanted, and concentrated in vacuo to give a light yellow foam. Flash chromatography on a 60 mm × 150 mm silica gel column eluting with 20% ethyl acetate/hexane to 75% ethyl acetate/hexane gave three fractions. Fraction #1, upon concentration, gave 330 mg (4.1%) of pure rapamycin-14,31,42-tris(monobenzylsuccinate).

$^1$H NMR (CDCl$_3$, 400 MHz) δ 7.353 (bs, 15 H, arom), 5.168 (d, J=2.0 Hz, 1 H, CH—O$_2$C), 5.148 (m, 6 H, CH$_2$Ph), 4.672 (m, 1 H, CO$_2$CH—CHOMe), 3.355 (s, 3 H, CH$_3$O—), 3.337 (s, 3 H, CH$_3$O—), 3.327 (s, 3 H, CH$_3$O—), 2.697 ( m, 12 H, O$_2$CCH$_2$CH$_2$CO$_2$CH$_2$Ph), 1.745 (s, 3 H, CH$_3$C=C), 1.655 (s, 3 H, CH$_3$C=C); IR (KBr) 3450 (OH), 2950 (CH), 1745 (C=O), 1650, 1460, 1385, 1360, 1160, 1105, 995 cm$^{-1}$.

Analysis Calcd. for C$_{84}$H$_{109}$NO$_{21}$.3 H$_2$O: C, 66.27; H, 7.56; N, 0.92. Found: C. 65.96; H. 7.24: N. 1.00.

The following representative compounds can be prepared from rapamycin and the appropriate half acid-ester by employing the method used to prepare the title compound in Example 1.

Rapamycin-14,31,42-tris(monomethylsuccinate)

Rapamycin-14,31,42-tris(monophenyl-3',3'-dimethylglutarate)
Rapamycin-14,31,42-tris(mono t-butyl-3'-methylglutarate)
Rapamycin-14,31,42-tris(monobenzylthiodiglycolate)
Rapamycin-14,31,42-tris(monohexyldiglycolate)
Rapamycin-14,31,42-tris(monopropylphthalate)
Rapamycin-14,31,42-tris(monoethyl-2',6'-pyridinedicarboxylate)

EXAMPLE 2

Rapamycin-31,42-bis(monobenzylsuccinate)

Fraction #2, obtained from the procedure employed in Example 1, gave 1.25 g (17.7%) of pure rapamycin-31,42-bis(monobenzylsuccinate) upon concentration.

$^1$H NMR (CDCl$_3$, 400 MHz) $\delta$7.351 (bs, 10 H, arom), 5.168 (d, J=2.0 Hz, 1 H, CH—O$_2$C), 5.125 (m, 4 H, CH$_2$Ph), 4.680 (m, 1 H, CO$_2$CH—CHOMe), 3.356 (s, 3 H, CH$_3$O—), 3.329 (s, 3 H, CH$_3$O—), 3.146 (s, 3 H, CH$_3$O—), 2.639 (m, 8 H, O$_2$CCH$_2$CH$_2$CO$_2$CH$_2$Ph), 1.748 (s, 3 H, CH$_3$C=C), 1.654 (s, 3 H, CH$_3$C=C); IR (KBr) 3450 (OH), 2940 (CH), 1740 (C=O), 1650, 1455, 1380, 1355, 1160, 1105, 995 cm$^{-1}$; MS (neg. ion FAB) 1294 (M-), 1202, 1103, 1012, 590, 511,475, 297, 207, 167, 148, 99 (100); High Res. MS (neg. ion FAB) Calcd for C$_{73}$H$_{99}$NO$_{19}$ 1293.68108, found 1293.6811.

Analysis Calcd. for C$_{73}$H$_{99}$NO$_{19}$·H$_2$O: C, 66.82; H, 7.70; N, 1.07. Found: C, 67.17; H, 7.67; N, 1.23.

The following representative compounds can be prepared from rapamycin and the appropriate half acid-ester by employing the method used to prepare the title compound in Example 2.
Rapamycin-31,42-bis(monomethylsuccinate)
Rapamycin-31,42-bis(monophenyl-3',3'-dimethylglutarate)
Rapamycin-31,42-bis(mono t-butyl-3'-methylglutarate)
Rapamycin-31,42-bis(monobenzylthiodiglycolate)
Rapamycin-31,42-bis(monohexyldiglycolate)
Rapamycin-31,42-bis(monopropylphthalate)
Rapamycin-31,42-bis(monoethyl-2',6'-pyridinedicarboxylate)

EXAMPLE 3

Rapamycin-42-(monobenzylsuccinate)

Fraction #3, obtained from the procedure employed in Example 1, gave 930 mg (15.4%) of pure rapamycin-42-monobenzylsuccinate upon concentration.

$^1$H NMR (CDCl$_3$, 400 MHz) $\delta$ 7.355 (bs, 5 H, arom), 5.141 (m, 2 H, CH$_2$Ph), 4.680 (m, 1 H, CO$_2$CH—CHOMe), 3.364 (s, 3 H, CH$_3$O—), 3.333 (s, 3 H, CH$_3$O—), 3.141 (s, 3 H, CH$_3$O—), 2.698 ( m, 4 H, O$_2$CCH$_2$CH$_2$CO$_2$CH$_2$Ph), 1.751 (s, 3 H, CH$_3$C=C), 1.655 (s, 3 H, CH$_3$C=C); IR (KBr) 3450 (OH), 2940 (CH), 1740 (C=O), 1645, 1455, 1380, 1165, 1105, 990 cm$^{-1}$; MS (neg. ion FAB) 1103 (M-), 1045, 1012, 624, 590, 167, 99 (100); High Res. MS (neg. ion FAB) Calcd for C$_{62}$H$_{89}$NO$_{16}$ 1103.6181, found 1103.6048.

Analysis Calcd. for C$_{62}$H$_{89}$NO$_{16}$·H$_2$O: C, 66.36; H, 8.02; N, 1.24. Found: C, 66.02; H, 7.69: N, 1.26.

The following representative compounds can be prepared from rapamycin and the appropriate half acid-ester by employing the method used to prepare the title compound in Example 3.
Rapamycin-42-monophenyl-3',3'-dimethylglutarate)
Rapamycin-42-(mono t-butyl-3'-methylglutarate)
Rapamycin-42-(monobenzylthiodiglycolate)
Rapamycin-42-(monohexyldiglycolate)
Rapamycin-42-(monopropylphthalate)
Rapamycin-42-(monoethyl-2',6'-pyridinedicarboxylate)

EXAMPLE 4

Rapamycin-31,42-bishemiglutarate

To a solution of 2.0 g (2.2 mmol) of rapamycin in 10 mL of dry dichloromethane was added 1.24 g (10.9 mmol) of glutaric anhydride followed by 881 uL (861 mg, 10.9 mmol) of pyridine. To this was added 200 mg of 4-dimethylaminopyridine and the reaction mixture was allowed to reflux for 8 h. The solution was cooled to room temperature, poured into 2N HCl, and extracted three times with dichloromethane. The combined organic extracts were washed with brine, dried over anhydrous sodium sulfate, decanted, and concentrated in vacuo to give a yellow foam. The crude product was purified via reverse phase HPLC on a C$_{18}$ column eluting starting with 60% acetonitrile/water. Collected, after, concentration, 586 mg (24%) of rapamycin-31,42-bishemiglutarate.

$^1$H NMR (CDCl$_3$, 400 MHz) $\delta$5.398 (m, 1 H, —CO$_2$CHCHOMe), 4.683 (m, 1 H, —CO$_2$CH-CHOMe), 3.364 (s, 3 H, CH$_3$O—), 3.362 (s, 3 H, CH$_3$O—), 3.106 (s, 3 H, CH$_3$O—), 2.407 (m, 8 H, —O$_2$CCH$_2$CH$_2$CH$_2$CO$_2$H), 1.960 (m, 4 H, —O$_2$CCH$_2$CH$_2$CH$_2$CO$_2$H), 1.770 (s, 3 H, CH$_3$C=C), 1.653 (s, 3 H, CH$_3$C=C); $^{13}$C NMR (CDCl$_3$, MHz) 211.45 (C=O), 206.84 (C=O), 200.44 (C=O), 177.83 (C=O), 177.04 (C=O), 172.43 (C=O), 171.20 (C=O), 165.27 (C=O), 159.08 (C=O); IR (KBr) 3430 (OH), 2940 (CH), 2880 (CH), 1745 (C=O), 1685, 1625, 1580, 1450, 1385, 1330, 1200, 1140, 1100, 990 cm$^{-1}$; MS (neg. ion FAB) 1140 (M-H), 1122, 1026, 990, 946, 913, 590, 475, 435, 321,167, 148, 131 (100), 113; High Res. MS (neg. ion FAB) Calcd for C$_{61}$H$_{90}$O$_{19}$N (M-H) 1140.6107, Found 1140.6106.

Analysis Calcd. for C$_{61}$H$_{91}$O$_{19}$N.H$_2$O: C, 63.15; H, 8.02; N, 1.20. Found: C, 63.35; H, 7.88; N, 1.40.

The following representative compounds can be prepared from rapamycin and the appropriate anhydride by employing the method used to prepare the title compound in Example 4.
Rapamycin-31,42-bishemi-3'-methylglutarate
Rapamycin-31,42-bishemi-3',3'-dimethylglutarate
Rapamycin-31,42-bishemi-3'-oxoglutarate
Rapamycin-31,42-bishemi-3'-thioglutarate
Rapamycin-31,42-bishemi-phthalate
Rapamycin-31,42-bishemi-2',3'-pyridine dicarboxylate

EXAMPLE 5

Rapamycin-31,42-hemiglutarate bissodium salt

Purified bis-31,42-hemiglutarate of rapamycin (740 mg, 649 umol), prepared as described in Example 4, was dissolved in 5 mL of 95% ethanol and 107 mg (1.27 mmol) of sodium bicarbonate was added. Water (1 mL) was added to completely dissolve the salt. Once dissolved, the light yellow solution was concentrated in vacuo to give a foamy yellow solid. The foam was dried in a drying pistol for 24 h, refluxing over acetone at reduced pressure to give 520 mg of the bissodium salt.

$^1$H NMR (d$_6$-DMSO, 400 MHz) $\delta$5.235 (m, 1 H, —CHO$_2$C), 4.498 (m, 1 H, MeOCHCHO$_2$C—), 3.287 (s, 6 H, 2 CH$_3$O—), 3.236 (s, 3 H, CH$_3$O—), 2.245 (m, 8 H, O$_2$CCH$_2$CH$_2$CH$_2$CO$_2$—), 1.712 (s, 3 H, CH$_3$C=C), 1.593 (s, 3 H, CH$_3$C=C); IR (KBr) 3420 (OH), 2920 (CH), 1725 (C=O), 1675, 1620, 1560, 1450, 1400, 1375, 1230, 1195, 1130, 1090, 980 cm$^{-1}$; MS (neg. ion FAB)

1112 (M-1, free acid), 994, 589, 475, 297, 167, 148, 117, 99 (100); High Res. MS (neg. ion FAB) Calcd for $C_{61}H_{89}O_{19}NNa$ (M-Na) 1162.5926, Found 1162.5899.

Analysis Calcd. for $C_{61}H_{89}O_{19}NNa_2 \cdot H_2O$: C, 60.85; H, 7.56: N, 1.16. Found: C, 60.67; H, 7.36: N, 1.58.

EXAMPLE 6

Rapamycin-31,42-bishemiglutarate bistromethamine salt

Purified bis-31,42 hemiglutarate of rapamycin (950 rag, 833 umol), prepared as described in Example 4, was dissolved in 5 mL of 95% ethanol and 197 mg 11.63 mmol) of tris(hydroxymethyl)methylamine was added. Water ( 1 mL) was added to completely dissolve the amine. Once dissolved, the yellow solution was concentrated in vacuo to give a foamy yellow solid. The very hygroscopic foam was dried in a drying pistol for 24 h, refluxing over acetone at reduced pressure to give 900 mg (78%) of the bistromethamine salt.

$^1$H NMR ($d_6$-DMSO, 400 MHz) δ 5.253 (m, 1 H, —CHO$_2$C), 4.523 (m, 1 H, MeOCHCHO$_2$C—), 3.347 (s, 6 H, 2 CH$_3$O—), 3.276 (s, 3 H, CH$_3$O—), 2.289 (m, 8 H, O$_2$CCH$_2$CH$_2$CH$_2$CO$_2$—), 1.681 (s, 3 H, CH$_3$C=C), 1.595 (s, 3 H, CH$_3$C=C); IR (KBr) 3400 (OH), 2920 (CH), 1730 (C=O), 1620, 1555, 1450, 1400, 1370, 1185, 1060, 980 cm$^{-1}$; MS (neg. ion FAB) 1140 (M-H, free acid), 1028, 167, 148, 131 (100), 113; High Res. MS (neg. ion FAB) Calcd for $C_{61}H_{90}O_{19}N$ (M-H, free acid) 1140.6107, Found 1140.6069.

Analysis Calcd. for $C_{69}H_{103}O_{25}N_3 \cdot 2H_2O$: C, 58.77; H, 7.58; N, 2.98. Found: C, 58.47; H, 7.94; N, 3.58.

EXAMPLE 7

Rapamycin-42-hemi-3'-oxoglutarate

To a solution of 3.0 g (3.3 mmol) of rapamycin in 20 mL of dry dichloromethane was added 1.90 g (16.4 mmol) of diglycolic anhydride followed by 1.32 mL (1.29 g, 16.4 mmol) of pyridine. To this was added 200 mg of 4-dimethylaminopyridine and the reaction mixture was allowed to stir at room temperature for 2 days. The solution was cooled to room temperature, poured into 2N HCl, and extracted three times with dichloromethane. The combined organic extracts were washed with brine, dried over anhydrous sodium sulfate, decanted, and concentrated in vacuo to give a yellow foam. The crude product was purified via reverse phase HPLC on a $C_{18}$ column eluting starting with 60% acetonitrile/water. After concentration, 870 mg( 26%) of rapamycin-42-hemi-3'-oxoglutarate and 500 mg (13%) of rapamycin-31,42-bishemi-3'oxoglutarate were isolated.

$^1$H NMR (CDCl3, 400 MHz) δ 4.768 (m, 1 H, CO$_2$-CH—CHOMe), 4.250 (m, 4 H, O$_2$CCH$_2$OCH$_2$CO$_2$), 3.356 (s, 3 H, CH$_3$O—), 3.331 (s, 3 H, CH$_3$O—), 3.139 (s, 3 H, CH$_3$O—), 1.759 (s, 3 H, CH$_3$C=C), 1.653 (s, 3 H, CH$_3$C=C); IR (KBr) 3420 (OH), 2920 (CH), 2875 (CH), 1740 (C=O), 1720 (C=O), 1640, 1625, 1445, 1370, 1320, 1200, 1135, 1095, 980 cm$^{-1}$; MS (neg. ion FAB) 1028 (M-H), 327, 167 (100), 148, 133, 115; High Res. MS (neg. ion FAB) Calcd for $C_{55}H_{82}O_{17}N$ M-H) 1028.5597, Found 1028.5599.

Analysis Calcd. for $C_{55}H_{83}O_{17}N \cdot 3 H_2O$: C, 60.97; H, 8.22: N, 1.29. Found: C, 61.33; H, 7.74: N, 1.69.

The following representative compounds can be prepared from rapamycin and the appropriate half acid-ester by employing the method used to prepare the title compound in Example 7.

Rapamycin-42-hemi-3'-methylglutarate
Rapamycin-42-hemi-3',3'-dimethylglutarate
Rapamycin-42-hemi-3'-thioglutarate
Rapamycin-42-hemi-phthalate
Rapamycin-42-hemi-2',3'-pyridine dicarboxylate

EXAMPLE 8

Rapamycin-31,42-bishemi-3'-oxoglutarate

To a solution of 5.0 g (5.47 mmol) of rapamycin in 20 mL of dry dichloromethane was added 3.17 g (27.3 mmol) of diglycolic anhydride followed by 2.17 mL (2.12 g, 27.3 mmol) of pyridine. To this was added 400 mg of 4-dimethylaminopyridine and the reaction mixture was allowed to stir at reflux for 24 h. The solution was cooled to room temperature, poured into 2N HCl, and extracted three times with dichloromethane. The combined organic extracts were washed with brine, dried over anhydrous sodium sulfate, decanted, and concentrated in vacuo to give a yellow foam. The crude product was purified via reverse phase HPLC on a $C_{18}$ column eluting starting with 60% acetonitrile/water. After concentration, 1.75 g (28%) of rapamycin-31,42-bishemi-3'-oxoglutarate was isolated.

$^1$H NMR (CDCl3, 400 MHz) δ 4.785 (m, 1 H, CO$_2$CHCHOMe), 4.260 (m, 8 H, O$_2$CCH$_2$OCH$_2$C$_2$), 3.360 (s, 3 H, CH$_3$O—), 3.343 (s, 3 H, CH$_3$O—), 3.143 (s, 3 H, CH$_3$O—), 1.775 (s, 3 H, CH$_3$C=C), 1.656 (s, 3 H, CH$_3$C=C); $^{-}$C NMR (CDCl3, MHz) 211.12 (C=O), 207.73 (C=O), 193.11 (C=O), 171.90 (C=O), 171.59 (C=O), 170.15 (C=O), 169.35 (C=O), 168.83 (C=O), 166.63 (C=O); IR (KBr) 3420 (OH), 2920 (CH), 2850 (CH), 1740 (C=O), 1645, 1625, 1440, 1370, 1190, 11300, 980 cm$^{-1}$; MS (neg. ion FAB) 1140 (M-H), 1122, 1026, 990, 946, 913, 590, 475, 435, 321,167, 148, 131 (100), 113; High Res. MS (neg. ion FAB) Calcd for $C_{59}H_{86}O_{21}N$ (M-H) 1144.5701, Found 1144.5702.

Analysis Calcd. for $C_{59}H_{87}O_{21}N$: C, 61.82; H, 7.65; N, 1.22. Found: C 61.59; H, 7.36; N, 1.84.

EXAMPLE 9

Rapamycin-31,42-bishemi-3'-oxoglutarate disodium salt

Purified bis-31,42 hemi-3'-oxoglutarate of rapamycin (720 mg, 629 umol), prepared by the procedure employed in Example 8, was dissolved in 10 mL of 95% ethanol and 106 mg (1.26 mmol) of sodium bicarbonate was added. Water (1 mL) was added to completely dissolve the salt. Once dissolved, the light yellow solution was concentrated in vacuo to give a foamy yellow solid. The foam was dried in a drying pistol for 48 h, refluxing over dichloromethane at reduced pressure to give 435 mg (58%) of the disodium salt.

$^1$H NMR ($d_6$-DMSO, 400 MHz) δ 4.975 (m, 1 H, —CHO$_2$C), 4.593 (m, 1 H, MeOCHCHO$_2$C—), 4.135 (s, 2 H, —O$_2$CCH$_2$OCH$_2$CO$_2$R), 3.617 (s,2 H, —O$_2$CCH$_2$OCH$_2$CO$_2$R), 3.299 (s, 6 H, 2 CH$_3$O—), 3.232 (s, 3 H, CH$_3$O—), 1.614 (s, 3 H, CH$_3$C=C), 1.553 (s, 3 H, CH$_3$C=C); IR (KBr) 3420 (OH), 2920 (CH), 1735 (C=O), 1615, 1445, 1395, 1380, 1320, 1220, 1130, 1090. 980 cm$^{-1}$; MS (neg. ion FAB) 1188 (M-1), 1166 (M-Na), 1144, 1051, 1028, 590, 459, 167, 155 (100), 148, 133, 115.

Analysis Calcd. for $C_{59}H_{85}O_{21}NNa_2 \cdot 2H_2O$: C, 57.79; H, 7.26: N, 1.14. Found: C, 57.94; H, 7.11; N, 1.26.

EXAMPLE 10

Rapamycin-31,42-bishemi-3'-oxoglutarate bistromethamine salt

Purified bis-31,42 hemi-3'-oxoglutarate of rapamycin (1.01 g, 882 umol), prepared by the procedure employed in Example 8, was dissolved in 10 mL of 95% ethanol and 213 mg (1.76 mmol) of tris(hydroxymethyl)-methylamine was added. Water (1 mL) was added to completely dissolve the amine. Once dissolved, the yellow solution was concentrated in vacuo to give a foamy yellow solid. The very hygroscopic foam was dried in a drying pistol for 48 h, refluxing over dichloromethane at reduced pressure to give 805 mg (66%) of the bistromethamine salt.

$^1$H NMR (d$_6$-DMSO, 400 MHz) δ 4.955 (m, 1 H, —CHO$_2$C), 4.600 (m, 1 H, MeOCHCHO$_2$C—), 4.149 (s, 2H, —O$_2$CCH$_2$OCH$_2$CO$_2$R), 3.770 (s, 2 H, —O$_2$CCH$_2$OCH$_2$CO$_2$R), 3.407 (s, 6 H, 2 CH$_3$O—), 3.257 (s, 3 H, CH$_3$O—), 1.806 (s, 3 H, CH$_3$C=C), 1.614 (s, 3 H, CH$_3$C=C); IR (KBr) 3400 (OH), 2920 (CH), 1730 (C=O), 1620, 1550, 1450, 1395, 1370, 1200, 1060, 985 cm$^{-1}$; MS (neg. ion FAB) 1144 (M-H, free acid), 1028, 167, 148, 133 (100), 115.

Analysis Calcd. for C$_{67}$H$_{109}$O$_{27}$N$_3$·H$_2$O: C, 57.22; H, 7.90; N, 2.98. Found: C, 57.26; H, 7.90; N, 3.15.

EXAMPLE 11

Rapamycin-31,42-bishemisuccinate

To a solution of 2.0 g (2.2 mmol) of rapamycin in 10 mL of dry dichloromethane was added 1.19 g (10.9 mmol) of succinic anhydride followed by 881 uL (861 mg, 10.9 mmol) of pyridine. To this was added 200 mg of 4-dimethylamino- pyridine and the reaction mixture refluxed for 24 h. The solution was cooled to room temperature, poured into 2N HCl, and extracted three times with dichloromethane. The combined organic extracts were washed with brine, dried over anhydrous sodium sulfate, decanted, and concentrated in vacuo to give a yellow foam. The crude product was purified via reverse phase HPLC on a C$_{18}$ column gradient eluting starting with 20% acetonitrile/water to 60% acetonitrile/water. Collected, after, concentration, 770 mg (31%) of rapamycin-31,42-bishemisuccinate.

The purified bis-31,42 hemisuccinate of rapamycin (770 mg, 686 umol) was dissolved in 10 mL of 95% ethanol and 166 mg (1.37 mmol) of tris(hydroxymethyl)methylamine was added. Water (1 mL) was added to completely dissolve the amine. Once dissolved, the yellow solution was concentrated in vacuo to give a foamy yellow solid. The very hygroscopic foam was dried in a drying pistol for 24 h, refluxing over acetone at reduced pressure to give 890 mg (95%) of the bistromethane salt. The bistromethane salt was evaluated in the standard pharmacological test procedures.

$^1$H NMR (d$_6$-DMSO, 400 MHz) 5.231 (m, 1 H, —CHO$_2$C), 4.554 (m, 1 H, MeOCHCHO$_2$C—), 3.426 (s, 6 H, 2 CH$_3$O—), 3.249 (s, 3 H, CH$_3$O—), 2.431 (m, 8 H, O$_2$CCH$_2$CH$_2$CO$_2$—), 1.700 (s, 3 H, CH$_3$C=C), 1.554 (s, 3 H, CH$_3$C=C); $^{13}$C NMR (d$_6$-DMSO,) 211.28 (C=O), 205.23 (C=O), 199.59 (C=O), 174.86 (C=O), 173.62 (C=O), 171.72 (C=O), 171.50 (C=O), 166.56 (C=O), 166.53 (C=O); IR (KBr) 3420 (OH), 2940 (CH), 1735 (C=O), 1630, 1580, 1460, 1400, 1380, 1170, 1070, 990 cm$^{-1}$; MS (neg. ion FAB) 1112 (M-1, free acid), 994, 589, 475, 297, 167, 148, 117, 99 (100).

Analysis Calcd. for C$_{67}$H$_{109}$O$_{25}$N$_3$·2 H$_2$O: C, 57.80; H, 8.12: N, 3.01. Found: C, 57.91; H, 8.21: N, 2.37.

EXAMPLE 12

Rapamycin-42-monomethylsuccinate

To a solution of 5.0 g (5.47 mmol) of rapamycin, 2.17 g (8.2 mmol) of monomethylsuccinate, and 1.58 g of 1-(3-dimethylaminopropyl)-3-ethylcarbodiimide hydrochloride in 20 mL of dry dichloromethane was added 100 mg of 4-dimethylaminopyridine. The solution was stirred at room temperature overnight. The reaction mixture was poured into 2N aqueous HCl and extracted three times with ethyl acetate. The organic layers were combined, washed with brine, dried over anhydrous sodium sulfate, filtered, and concentrated in vacuo to give a viscous yellow oil. Flash chromatography on a 60 mm×150 mm silica column eluting with 20% ethyl acetate/hexane to 40% ethyl acetate/hexane gave 2.35 g (42%) of pure rapamycin-42-monomethylsuccinate.

$^1$H NMR (CDCl$_3$, 400 MHz) δ 4.79 (s, 1 H, —OH), 4.69 (bm, 1 H, 42—CHOC=O), 3.69 (s, 3 H, CH$_3$OC=O), 3.38 (s, 3 H, CH$_3$O—), 3.33 (s, 3 H, CH$_3$O—), 3.14 (s, 3 H, CH$_3$O—), 2.64 (m, 4 H, O=CCH2CH2C=O); IR (KBr) 3440 (OH), 2930 (CH), 1735 (C=O), 1720 (C=O), 1643, 1445, 1375, 1160, 1090, 990 cm$^{-1}$; MS (neg. ion FAB) 1027 (M-), 590.

Analysis Calcd. for C$_{56}$H$_{85}$NO$_{16}$·3 H$_2$O: C, 62.14; H, 8.48; N, 1.29. Found: C, 61.98; H, 7.60; N, 1.21.

EXAMPLE 13

Rapamycin-42-(4-trifluoromethylbenzyl)succinate

To a solution of 5.0 g (5.47 mmol) of rapamycin, 2.26 g (8.2 mmol) of mono(4-trifluoromethylbenzyl)succinate, and 1.58 g of 1-(3-dimethylaminopropyl)-3-ethylcarbodiimide hydrochloride in 20 mL of dry dichoromethane was added 100 mg of 4-dimethylaminopyridine. The solution was stirred at room temperature overnight. The reaction mixture was poured into 2N aqueous HCl and extracted three times with ethyl acetate. The organic layers were combined, washed with brine, dried over anhydrous sodium sulfate, filtered, and concentrated in vacuo to give a viscous yellow oil. Flash chromatography on a 60 mm×150 mm silica column eluting with 10–20% ethyl acetate/hexane gave 365 mg (6%) of pure rapamycin-42-(4-trifluoromethylbenzyl)succinate.

$^1$H NMR (CDCl$_3$, 400 MHz) δ 7.46–7.63 (ab, 4 H, arom), 5.19 (m, 2 H, CH$_2$Ar), 4.79 (s, 1 H, —OH), 4.68 (bm, 1 H, 42—CHOC=O), 3.36 (s, 3 H, CH$_3$O—), 3.33 (s, 3 H, CH$_3$O—), 3.14 (s, 3 H, CH$_3$O—), 2.71 (m, 4 H, O=CCH2CH2C=O); IR (KBr) 3445 (OH), 2940 (CH), 1740 (C=O), 1720 (C=O), 1650, 1450, 1375, 1330, 1160, 1060, 990 cm$^{-1}$; MS (neg. ion FAB) 1171 (M-), 1012, 590.

Analysis Calcd. for C$_{63}$H$_{88}$NO$_{16}$F$_3$·H$_2$O: C, 63.56; H, 7.62: N, 1.18. Found: C, 63.34; H, 7.31: N, 1.28.

EXAMPLE 14

Rapamycin-42-allylglutarate and

EXAMPLE 15

Rapamycin-31-allylglutarate

To a solution of 500 mg (547 μmol) of rapamycin, 141 mg (820 μmol) of monoallylglutaric acid, and 158 mg of 1-(3-dimethylaminopropyl)-3-ethylcarbodiimide hydrochloride in 5 mL of dry dichoromethane was added 10 mg of 4-dimethylaminopyridine. The solution was stirred at room temperature overnight. The reaction mixture was poured into water and extracted three times with ethyl acetate. The organic layers were combined, washed with brine, dried over anhydrous sodium sulfate, filtered, and concentrated in vacuo to give a viscous yellow oil. Reverse phase HPLC chromatography (1" Dynamax phenyl column, 70% MeCN/H2O, 6 mL/min) gave three fractions: rapamycin, 154 rag; rapamycin-31-allylglutarate, 81 mg: and rapamycin-42-allylglutarate, 121 mg.

Spectral data follows for rapamycin-42-monoallylglutarate. $^1$H NMR (DMSO-d$_6$, 400 MHz) δ 5.86 (m, 1 H, —CH═CH$_2$), 5.25 (m, 2 H, —CH═CH$_2$), 4.55 (bin, 1 H, 42—CHOC═O), 4.50 (d, 2 H, CH$_2$CH═CH$_2$), 3.31 (s, 3 H, CH$_3$O—), 3.25 (s, 3 H, CH$_3$O—), 3.15 (s, 3 H, CH$_3$O—), 2.49 (m, 2 H, O═CCH$_2$CH$_2$CH$_2$C═O), 2.38 (m, 4 H, O═CCH$_2$CH$_2$CH$_2$C═O); IR (KBr) 3440 (OH), 2925 (CH), 1730 (C═O), 1720 (C═O), 1643, 1447, 1372, 1185, 1090, 985 cm$^{-1}$; MS (neg. ion FAB) 1067 (M-), 590, 475.

Analysis Calcd. for $C_{59}H_{89}NO_{16} \cdot H_2O$: C, 65.25; H, 8.39; N, 1.29. Found: C, 65.28; H, 8.29; N, 1.39.

Spectral data follows for rapamycin-31-monoallylglutarate. $^1$H NMR (CDCl$_3$, 400 MHz) δ 5.89 (m, 1 H, —CH═CH$_2$), 5.25 (m, 2 H, —CH═CH$_2$), 5.20 (m, 1 H, 31—CHOC═O), 4.54 (d, 2 H, CH$_2$CH═CH$_2$), 3.31 (s, 3 H, CH$_3$O—), 3.19 (s, 3 H, CH$_3$O—), 3.04 (s, 3 H, CH$_3$O—), 2.49 (m, 2 H, O═CCH$_2$CH$_2$CH$_2$C═O), 2.32 (m, 4 H, O═CCH$_2$CH$_2$CH$_2$C═O); IR (KBr) 3440 (OH), 2930 (CH), 2860, 1735 (C═O), 1720 (C═O), 1640, 1445, 1372, 1185, 1160, 1135, 1080, 985 cm$^{-1}$; MS (neg. ion FAB) 1067 (M-), 590, 475.

Analysis Calcd. for $C_{59}H_{89}NO_{16} \cdot 2H_2O$: C, 64.19; H, 8.43; N, 1.27. Found: C, 64.29; H, 8.12; N, 1.21.

What is claimed is:

1. A compound of the structure

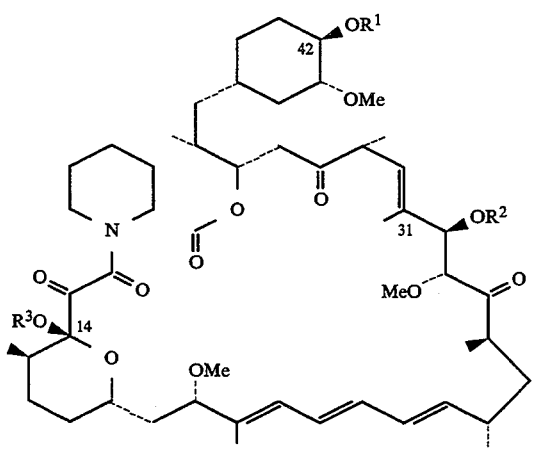

wherein $R^1$, $R^2$, and $R^3$ are each, independently, hydrogen or

with the proviso that $R^1$, $R^2$, and $R^3$ are not all hydrogen;

$R^4$ is —(CH$_2$)$_m$X(CH$_2$)$_n$CO$_2$R$^5$ or

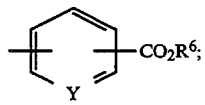

$R^5$ and $R^6$ are each, independently, hydrogen, alkenyl of 2-7 carbon atoms, alkynyl of 2-7 carbon atoms, (CH$_2$)$_p$NR$^9$R$^{10}$, mono-, di-, or tri-hydroxyalkyl of 1-8 carbon atoms, or aryl, which is optionally mono-, di-, or tri- substituted with a group selected from alkyl of 1-6 carbon atoms, arylalkyl of 7-10 carbon atoms of which the alkyl group is of 1-4 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, and alkylthio of 1-6 carbon atoms, wherein the above aryl group is selected from phenyl, pyridinyl, thienyl, furyl, isoxazolyl, thiazolyl, imidazolyl, pyrazinyl, pyrimidinyl, benzofuryl, benzoxazolyl, benzoisoxazolyl, benzthiazolyl, benimidazolyl, indolyl, quinolyl, isoquinolyl, thianaphthyl and benzopyranyl;

X is

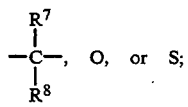

$R^7$, $R^8$, $R^9$, and $R^{10}$ are each, independently, hydrogen or alkyl of 1-6 carbon atoms:

Y is CH or N:

m is 0-4;

n is 0-4:

p is 0-4;

with the proviso that m and n are not both 0 when X is O or S;

or a pharmaceutically acceptable salt thereof.

2. A compound of claim 1 where $R^4$ is —(CH$_2$)$_m$X (CH$_2$)$_n$ CO$_2$R$^5$ or a pharmaceutically acceptable salt thereof.

3. A compound of claim 2 wherein $R^5$ is alkenyl of 2-7 carbon atoms or a pharmaceutically acceptable salt thereof.

4. A compound of claim 1 which is rapamycin-42-allylglutarate or a pharmaceutical salt thereof.

5. A compound of claim I which is rapamycin-31-allylglutarate or a pharmaceutical salt thereof.

6. A pharmaceutical composition for use as an immunosuppressive agent comprising an immunosuppressive amount of a compound having the structure

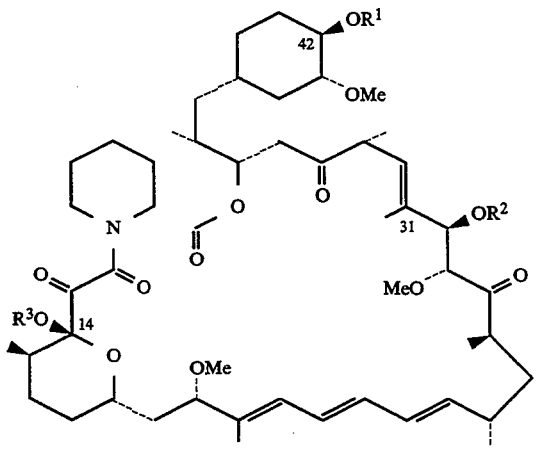

wherein

R¹, R², and R³ are each, independently, hydrogen or

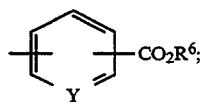

with the proviso that R¹, R², and R³ are not all hydrogen;

R⁴ is —(CH₂)$_m$X(CH₂)$_n$CO₂R⁵ or

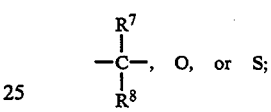

R⁵ and R⁶ are each, independently, hydrogen, alkenyl of 2–7 carbon atoms, alkynyl of 2–7 carbon atoms, (CH₂)$_p$NR⁹R¹⁰, mono-, di-, or tri-hydroxyalkyl of 1–8 carbon atoms, or aryl, which is optionally mono-, di-, or tri- substituted with a group selected from alkyl of 1–6 carbon atoms, arylalkyl of 7–10 carbon atoms of which the alkyl group is of 1–4 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, and alkylthio of 1–6 carbon atoms wherein the above aryl group is selected from phenyl, pyridinyl, thienyl, furyl, isoxazolyl, thiazolyl, imidazolyl, pyrazinyl, pyrimidinyl, benzofuryl, benzoxazolyl, benzoisoxazolyl, benzthiazolyl, benimidazolyl, indolyl, quinolyl, isoquinolyl, thianaphthyl and benzopyranyl;

X is $$-\underset{R^8}{\overset{R^7}{\underset{|}{\overset{|}{C}}}}-, \text{ O, or S};$$

R⁷, R⁸, R⁹, and R¹⁰ are each, independently, hydrogen or alkyl of 1–6 carbon atoms:

Y is CH or N;

m is 0–4;

n is 0–4;

p is 0–4;

with the proviso that m and n are not both 0 when X is O or S;

or a pharmaceutically acceptable salt thereof, and a pharmaceutical carrier.

* * * * *